US009308101B2

(12) United States Patent
Doty (10) Patent No.: US 9,308,101 B2
(45) Date of Patent: Apr. 12, 2016

(54) SHOCK ABSORBING, TOTAL DISC REPLACEMENT PROSTHETIC DEVICE (71) Applicant: TRUEMOTION SPINE, INC., Gainesville, FL (US)

(72) Inventor: Keith L. Doty, Gainesville, FL (US)

(73) Assignee: TrueMotion Spine, Inc., Gainesville, FL (US)

( * ) Notice: Subject to any disclaimer, the term of this patent is extended or adjusted under 35 U.S.C. 154(b) by 0 days.

(21) Appl. No.: 14/433,494

(22) PCT Filed: Oct. 22, 2013

(86) PCT No.: PCT/US2013/066126
§ 371 (c)(1),
(2) Date: Apr. 3, 2015

(87) PCT Pub. No.: WO2014/066354
PCT Pub. Date: May 1, 2014

(65) Prior Publication Data
US 2015/0223949 A1 Aug. 13, 2015

Related U.S. Application Data (60) Provisional application No. 61/717,709, filed on Oct. 24, 2012.

(51) Int. Cl.
A61F 2/44 (2006.01)
A61F 2/30 (2006.01)

(52) U.S. Cl.
CPC .............. A61F 2/4425 (2013.01); A61F 2/442 (2013.01); A61F 2002/305 (2013.01); A61F 2002/3049 (2013.01); A61F 2002/30069 (2013.01); A61F 2002/30115 (2013.01); A61F 2002/30125 (2013.01); A61F 2002/30138 (2013.01); A61F 2002/30153 (2013.01); A61F 2002/30154 (2013.01); A61F 2002/30158 (2013.01); A61F 2002/30159 (2013.01); A61F 2002/30235 (2013.01); A61F 2002/30331 (2013.01); A61F 2002/30364 (2013.01); A61F 2002/30367 (2013.01); A61F 2002/30369 (2013.01); A61F 2002/30372 (2013.01); A61F 2002/30373 (2013.01); A61F 2002/30375 (2013.01); A61F 2002/30387 (2013.01); A61F 2002/30448 (2013.01); A61F 2002/30454 (2013.01); A61F 2002/30474 (2013.01); A61F 2002/30495 (2013.01); A61F 2002/30518 (2013.01); A61F 2002/30546 (2013.01); A61F 2002/30548 (2013.01); A61F 2002/30563 (2013.01); A61F 2002/30581 (2013.01); A61F 2002/30621 (2013.01); A61F 2002/30673 (2013.01); A61F 2002/30845 (2013.01); A61F 2002/30971 (2013.01); A61F 2002/443 (2013.01); A61F 2310/00023 (2013.01)

(58) Field of Classification Search
CPC .. A61F 2/442; A61F 2/4425; A61F 2002/443
See application file for complete search history.

(56) References Cited

U.S. PATENT DOCUMENTS

| 5,507,816 A | 4/1996 | Bullivant |
| 5,676,701 A | 10/1997 | Yuan et al. |
| 5,782,832 A | 7/1998 | Larsen et al. |
| 6,368,350 B1 | 4/2002 | Erickson et al. |
| 6,582,466 B1 | 6/2003 | Gauchet |
| 6,582,468 B1 | 6/2003 | Gauchet |
| 2002/0035400 A1* | 3/2002 | Bryan ..................... A61B 17/02 623/17.15 |
| 2003/0069643 A1* | 4/2003 | Ralph ..................... A61F 2/4425 623/17.13 |
| 2003/0204261 A1* | 10/2003 | Eisermann ............. A61F 2/4425 623/17.14 |
| 2004/0133278 A1* | 7/2004 | Marino .................. A61F 2/4425 623/17.14 |
| 2004/0167626 A1 | 8/2004 | Geremakis et al. |
| 2007/0173936 A1 | 7/2007 | Hester et al. |
| 2010/0070033 A1 | 3/2010 | Doty |
| 2010/0082110 A1 | 4/2010 | Belliard |
| 2010/0324688 A1 | 12/2010 | Doty |

* cited by examiner

Primary Examiner — Anu Ramana
(74) Attorney, Agent, or Firm — Saliwanchik, Lloyd & Eisenschenk (57) ABSTRACT A hybrid mechanical device comprising rigid-body joints, such as rotational and planar joints, and one or more continuum joints that operate based on constitutive properties of materials, such as, for example, flexure, extension and compression. Embodiments include a tripartite nucleus comprising a cap, core, and sled. The cap is rotatably connected to a first end plate and the sled is rotationally and translationally connected to a second end plate. The joint surfaces between the nucleus and end plates of the device provide up to six degrees of freedom. The constitutive properties of the core can further provide a "continuum" joint to complete the hybrid mechanical motion producing structure. In certain embodiments, the cap, core and sled comprise the same or substantially the same material. But, in other embodiments, the cap, core and sled comprise different materials.

19 Claims, 9 Drawing Sheets

SHOCK ABSORBING, TOTAL DISC REPLACEMENT PROSTHETIC DEVICE

CROSS-REFERENCE TO RELATED APPLICATIONS

This application is the U.S. national stage application of International patent application no. PCT/US2013/066126, filed Oct. 22, 2013, which claims the benefit of U.S. Provisional Application Ser. No. 61/717,709, filed Oct. 24, 2012, the disclosures of which are hereby incorporated by reference in their entireties, including any figures, tables, or drawings.

BACKGROUND OF INVENTION

Spinal disc herniation, a common ailment, and degenerative disc disease often induce pain, as well as neurologically and physiologically debilitating consequences, for which relief becomes paramount. If conservative treatments fail, the more drastic measures of discectomies and spinal fusion may be indicated. The latter treatment, while providing short term relief, limits spinal mobility and often leads to excessive forces on facet joints adjacent to the fusion and may create further problems over time. Drastic treatments are usually unable to restore normal disc function. The loss of disc function has led to a number of disc prostheses that attempt to provide natural motion.

The literature documents that the Instantaneous Axis of Rotation (IAR) during sagittal rotation of the superior vertebra with respect to the inferior vertebra of a Functional Spinal Unit (FSU) in the cervical spine moves significant distances during flexion and extension of the spine (Mameren, H. van, Sanches, H., Beursgens, J., Drukker, J., "Cervical Spine Motion in the Sagittal Plane II: Position of Segmental Averaged Instantaneous Centers of Rotation—A Cineradiographic Study", *Spine* 1992, Vol. 17, No. 5, pp. 467-474). This motion can vary widely between functional spinal units on an individual spine and between individuals and can depend on a variety of factors, including age, time-of-day, and the general health and condition of the intervertebral discs, the facet joints and other components of the FSU and spine. A moving IAR means that the superior vertebra is both rotating and translating, while moving with respect to the inferior vertebra of an FSU.

Researchers have attempted to design a successful intervertebral disc replacement for years. Salib et al., U.S. Pat. No. 5,258,031; Marnay, U.S. Pat. No. 5,314,477; Boyd et al., U.S. Pat. No. 5,425,773; Yuan et al., U.S. Pat. No. 5,676,701; and Larsen et al., U.S. Pat. No. 5,782,832 all use ball-and-socket arrangements fixed to the superior and inferior plates, which are rigidly attached to the vertebrae of an FSU. However, these designs tend to limit motion to rotation only about the socket when the ball-and-socket components of the two plates are in contact. As the literature points out (Bogduk N. and Mercer S., "Biomechanics of the cervical spine. I: Normal kinematics", *Clinical Biomechanics, Elsevier*, 15(2000) 633-648; and Mameren, H. van, Sanches, H., Beursgens, J., Drukker, J., "Cervical Spine Motion in the Sagittal Plane II: Position of Segmental Averaged Instantaneous Centers of Rotation-A Cineradiographic Study", *Spine* 1992, Vol. 17, No. 5, pp. 467-474), this restricted rotational motion does not correspond to the natural motion of the vertebrae, either for sagittal plane motion or for combined sagittal, lateral and axial motion. Further, when the ball-and-socket arrangements on the two plates, as described in the above-cited patents, are not in contact, the devices are unable to provide stability to the intervertebral interface, which can allow unnatural motions and lead to disc related spondylolisthesis, FSU instability, and excessive facet loading.

Advances in disc arthroplasty design have resulted from intense research and patent activity in this field. Duggal in U.S. Pat. No. 7,927,374B2, for example, discloses a design comprising a nucleus between two endplates possessing articulating surfaces with two endplates. Other researchers and designers have disclosed similar structures fitting such a general description, such as for example: Bullivant, U.S. Pat. No. 5,507,816; Erickson, U.S. Pat. No. 6,368,350; Gauchet, U.S. Pat. No. 6,527,804; and Cohen et al. U.S. Pat. No. 7,282,063. However, the nuclei in these examples do not couple flexure joint action with mechanical articulation.

Motion coupling between flexion-extension, axial rotation, and lateral bending and other functional spinal units involved in the overall spinal motion, increases the complexity and difficulty in developing a prosthetic disc replacement that realizes natural spinal motion. Producing such complex disc motions with strictly articulating joints is at best problematic. Alternatives that utilize only a flexible core or nucleus between two plates to solve the problem of disc motion requirements is also not a new idea. Stubstad et al. U.S. Pat. No. 3,867,728 proposes an elastic polymer between plates. Other patents provide similar instruction, for example, see Fuhrmann et al., U.S. Pat. No. 5,002,576 and Baumgartner U.S. Pat. No. 5,370,697. New designs, such as the Spinal Kinetics M6 device based on Reo et al., and U.S. Pat. No. 7,731,753, have been developed.

Additional motion complexity required of a spinal disc derives from motion constraints dictated by facet joints. Complex facet joint surfaces in an FSU can significantly influence and constrain sagittal, lateral and axial motions. The orientation of these facet surfaces varies with FSU location in the spine and allows for wide variations in motion parameters and constraints. The complex motion of a superior vertebra with respect to the associated inferior vertebra of an intact spinal joint segment, certainly in the cervical spine, cannot be realized by a simple rotation or simple translation, or even a combination of rotation and translation along a fixed axis, and still maintain the integrity and stability of the spinal segment, in particular the facet joints.

Natural spinal motions, therefore, can place severe requirements on the design of a prosthetic disc, such that a minimum of six independent degrees of freedom is usually required to achieve full naturalized mobility. The number of independent mechanical degrees of freedom of a disc modeled on rigid body assumptions, however, can be undesirably reduced by one or more degrees of freedom with the use of one or more joint stops or other singularities of configuration, thus limiting further motion along or within the range of motion of the reduced degrees of freedom. Using only mechanically articulating joints, therefore, can be problematic in resolving complex disc motion. Adding flexure motion capability between relatively rigid mechanical joints within a disc prosthesis can enhance the prosthesis responsiveness when in configurations that restrict certain motions of mechanical articulating joints. On the other hand, mechanical articulating joints can provide structurally stronger and more robust motion generation with less stress. A combination of articulating joints and flexure motion structures within this invention disclosure, therefore, takes advantage of each type of joint. This combination of mechanical and flexural joints represents a hybrid disc prosthetic system, hybrid because it employs both rigid-body articulating joints and flexure joints A natural spinal joint responds to spinal muscle controls primarily through flexure of the disc and mechanical articulation of synovial facet joints. Bone structures, tendons and muscles of a spinal joint also influence spinal joint motion.

These complex interactions have yet to be modeled to any degree of accuracy, although progress is being made.

Some recent patents and published applications relating to spinal disc prostheses incorporating flexible elements between endplates in an attempt to emulate natural disc behavior without articulating joints are U.S. Pat. Nos. 8,377, 138B2; 7,857,852B2; and U.S. Published Patent Application No. 20090270988A1. While these solutions provide more variability in motion, they are limited in the range of motions provided in any given direction and they do not have the robustness engendered by the use of mechanical elements.

There is a need in the art for a spinal disc prosthetic device that can provide all desired degrees of freedom and natural ranges of motion. Specifically, a device is needed that combines articulating mechanical joints and material flexure in a unique way to accommodate complex spine joint motion. Such a device will solve certain natural motion and shock absorbing characteristics that are problematic for spinal disc prostheses and offer a scalable mechanism for disc replacement without loss of general motion capabilities.

Specific embodiments of such a device might utilize a flexure material that articulates with one or more plates as an integrated whole, and could even possess gradients in mechanical moduli and material structure. In a further ideal, the flexure material would be moveably locked between the plates so as to resist expulsion and separation of the unit. Specifically, the geometry and material properties of the flexure material can couple with the mechanical articulating joints in a fundamental manner that can allow complementary rotations and translations and can, preferably, resist such motions by generating reaction forces and moments-of-force to torsions, compressions, extensions, and bending, as a consequence of its material properties.

Thus, there is a need for a hybrid joint system, being one that employs rigid-body-modeled, articulating, mechanical joints with a non-rigid body flexure nucleus between mechanical joints, which can perform complex, coupled motions required of a natural disc.

The invention herein discloses devices that can perform such complex motions without knowing the precise motion trajectories produced by a natural disc. Specifically, articulating mechanical joints of the invention can provide four independent degrees of freedom. Flexure of the nucleus between the two mechanical joints, allows a continuum of motions within the rated modulus of the material. In particular, flexure in the invention accommodates compression-extension and lateral bending motions along the axial axis of the FSU independent of the articulation joint degrees of freedom.

SUMMARY OF THE INVENTION

The devices and methods of the subject invention address the above-described disadvantages associated with previously known devices and methods. The embodiments described herein provide novel and highly effective methods and implantable mechanical devices for replacement of one or more spinal discs.

When implanted in a functional spinal unit (FSU), the devices of the subject invention can provide up to six independent degrees of freedom relative to a neutral position and enables the FSU to exercise complex motions dictated by spinal muscles, including motions consisting of simultaneous, compound rotations coupled with simultaneous multi-axis translations. A moving Instantaneous Axis of Rotation (IAR), typically dictated by flexion and extension in the cervical spine, for example, can be successfully tracked by the devices of the invention, by utilizing both a movable rotation center and appropriate multi-axis translations. Certain embodiments of the invention also provide shock absorption.

Certain devices of the invention utilize a unique hybrid mechanical system comprising rigid-body joints, such as rotational and planar joints, and, in other embodiments, one or more continuum joints that operate based on constitutive properties of materials, such as, for example, flexure, extension and compression. This principle of a hybrid mechanical system can be extended to include a plurality of rigid-body joints combined with a plurality of continuous joints based on constitutive properties of various materials, such as, but not limited to, flexible polymers or elastomers.

In certain embodiments, the devices of the subject invention comprise a first and second endplate each with first and second end surfaces, and a tripartite nucleus, between the first and second endplates. The tripartite nucleus can comprise a cap, core, and sled, each with first and second end surfaces and can comprise combinations of materials, both rigid and flexible. A first endplate can provide a first end surface with features that allow fusion of the first endplate to a first vertebra of a FSU. A second endplate can provide a second end surface with features that allow fusion of the second endplate to a second vertebra of an FSU. Several endplate geometries are exemplified herein. For example, the perimeter defined by a horizontal planar section of an endplate can be a general closed planar curve of which a circle, ellipse, and rounded-corners squares, rectangles, and trapezoids can describe simple instances.

The tripartite nucleus is operably connected to the end plates, such that the cap is operably connected to a first end plate and the sled is operably connected to a second end plate. The first end plate can have multi-curvate, multi-concave, and multi-convex surfaces that conform and mate to the first end surface of the cap to form a mechanical joint that can produce at least one degree, and up to three degrees, of rotational freedom. Conversely, the second end plate can have a cavity that can mate to a sled and produce at least one translational degree of freedom and up to two translational degrees of freedom and one rotational degree of freedom.

Additionally a core can be positioned between the end plates. Embodiments of the core allow vertical translation through compression or extension of the material and left-lateral and right-lateral bending through flexure. These motions can provide the complete six degrees of freedom possible with embodiments of the invention. The constitutive properties of the core, therefore, provide a "continuum" joint to complete the hybrid mechanical motion producing structure of these invention embodiments. In certain embodiments, the cap, core and sled comprise the same or substantially the same material. But, in other embodiments, the cap, core and sled comprise different materials.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to, or implication of, dimensions in the drawings or the following description are specific to the embodiments disclosed. Any variations of these dimensions that allow the subject invention to function for its intended purpose are within the scope of the subject invention. Thus, understanding that these drawings depict only typical embodiments of the invention and are not therefore to be considered as limiting in scope, the invention will be described and explained with additional specificity and detail through the use of the accompanying drawings in which:

FIG. 1 illustrates a left-anterior perspective view of an embodiment of the invention with an optional boot 13-1, or sheath, surrounding the nucleus of the device. In this embodiment, the beads 13-1-1 and 13-1-2 on the boot fit and lock into conforming groves on the first endplate 1-1 and the second endplate 5-1. Projections 1-1-1 on a first end surface 1-1-2 of a first endplate 1-1 can penetrate a first vertebra and can help retain the plate within the intervertebral space by engaging bone. Curvate first end surface 1-1-2 of a first endplate can be treated in a number of ways, which would be understood by those skilled in the art to encourage bone fusion.

FIG. 2 shows a perspective, primarily left-lateral view, of an embodiment of the invention without a boot as seen from slightly above and anterior to the device's left lateral side, wherein only core 3-1 of the nucleus can be observed. Rotational joint stops 1-1-3 and 1-1-4, of this embodiment, limit the amount of relative rotation of first endplate 1-1 with respect to the nucleus. A retaining feature 1-1-5 on both lateral surfaces of the first endplate can comprise multi-curvate, inward pointing projections that can rotationally lock the first endplate to the cap of the nucleus The retaining features can allow rotation of the cap in an anterior to posterior direction or along the sagittal plane. Projections 5-1-1 on a second end surface of a snap-fitting second endplate 5-1 embodiment penetrate a second vertebra and can help retain the plate within the intervertebral space by engaging bone. The curvate second end surface 5-1-2 of the snap-fitting second endplate 5-1 can be treated in a number of ways, known to those skilled in the art, to encourage bone fusion.

FIG. 3 is a perspective, central sagittal-plane cross-sectional view of FIG. 2 revealing features of an embodiment of the tripartite nucleus 14, which are: a cap 2-1, a core 3-1, and a sled 4-1, of a particular embodiment of the invention. A coordinate frame $F_1$ with coordinate axes 7, 8, 9, or $x_1, y_1, z_1$ axes, respectively, defines the sagittal, axial, and frontal axes, respectively, of a frame attached to the first endplate. A coordinate frame $F_2$ with coordinate axes 10, 11, 12, or $x_2, y_2, z_2$ axes, defines the sagittal, axial, and frontal axes, respectively, of a frame attached to the second endplate. The sled 4-1 can be disc shaped and fit into and be retained within an oversized second endplate cavity 5-4 within the first end surface of the snap-fitting second endplate 5-1. This configuration can allow translation of the sled in any radial direction 5-2-3 from the cavity center and free rotation about center axis 14-1 of the nucleus, which extends perpendicular to, and at the geometric center of, the plane of the second surface of the sled (FIG. 14) and extends through the geometric center of the cap. The sled 4-1 can be designed to be retained with a snap fit into the second endplate cavity.

FIG. 8 is an exploded view of the embodiment shown in FIG. 2. Multiple-convex surface retaining features of 1-1-5 and the large concave curvate chamber 1-1-10 in the second end surface of the first endplate 1-1 can be seen here.

FIG. 9 is an exploded view of the embodiment shown in FIG. 4. In this embodiment, retaining ring 6-1 has an aperture 6-1-1 of sufficient size to allow the retaining ring to pass by or traverse core 3-1. The inner diameter of the retaining ring 6-1 can be smaller than the sled diameter to prevent the sled or the cap from exiting the cavity 5-4.

FIG. 13 illustrates a sagittal exploded view of an embodiment of a tripartite nucleus 14 emphasizing the slope 3-1-5, or lordosis angle of the first end planar surface and the second end planar surface of the core, 3-1-1 (FIGS. 15) and 3-1-2 (FIG. 14), respectively.

FIG. 14 depicts an exploded below-front-left side perspective view of an embodiment of a tripartite nucleus 14. The concave curvate surfaces 2-1-3 within a notch 2-1-5 in a second end surface of the cap 2-1 can have the same center of curvature as the convex curvate surface 2-1-1 (FIG. 15) on the first end surface of the cap 2-1. Cap second end surface can also have a planar surface 2-1-2 that fixedly attaches to, or integrates with, core first end surface 3-1-1 (FIG. 15). Lateral planar surface 2-1-4 can also bound one end of the concave curvate surface 2-1-3. The core can have an optional bore 3-1-3 and a curvate lateral surface 3-1-4 as well as planar first and second end surfaces 3-1-1 and 3-1-2.

The first end surface 4-1-1 of the sled can be planar. Each element of the tripartite nucleus can be of a different polymer or other material. Alternatively, each element can be comprised of all the same polymer as an integrated homogenous unit.

DETAILED DISCLOSURE

The following description will disclose embodiments of the subject invention that are useful in the medical fields encompassing spinal surgery and, in particular, to devices and methods for correcting, replacing, or approximating movement between two vertebrae within a spine, i.e., a Functional Spinal Unit (FSU).

More specifically, the embodiments disclosed herein are useful for the treatment and/or removal of spinal disc herniation and degenerative disc disease. A person with skill in the art will be able to recognize other uses that would be applicable to the devices and methods of the subject invention.

While the subject application describes, and many of the terms herein relate to, a use for installation within a spine, particularly for the treatment of spinal disc herniation and degenerative disc disease, other uses and modifications thereof that will be apparent to a person with skill in the art and having benefit of the subject disclosure are contemplated to be within the scope of the present invention.

In the description that follows, a number of terms are used in relation to the spine, spinal surgery, and medical devices related thereto. In order to provide a clear and consistent understanding of the specification and claims, including the scope to be given such terms, the following definitions are provided:

The term "Functional Spinal Unit" or "FSU", as used herein, refers to a physiological unit of a spine that includes two adjacent vertebrae, an intervertebral disc and all naturally occurring adjoining ligaments between the vertebrae. An FSU typically does not include connecting tissues, such as muscles, vascular tissue, such as veins or arteries, or nerve tissue.

The term "corresponding elements" of the subject invention refers to variations in the design of an element wherein the variations have the same or similar function and possess many of the same features.

The term "patient" as used herein, describes an animal, including mammals, to which the systems and methods of the present invention can be applied. Mammalian species that can benefit from the disclosed systems and methods include, but are not limited to, apes, chimpanzees, orangutans, humans, and monkeys; domesticated animals (e.g., pets) such as dogs, cats, guinea pigs, and hamsters; veterinary uses for large animals such as cattle, horses, goats, and sheep; and any wild animal for veterinary or tracking purposes.

Also, the terms top and bottom can be substituted for the terms first and second to clarify the descriptions, but this does not imply any specific or required orientation for the device. Thus, the device could be turned such that one could refer to bottom and top for first and second as well. Therefore, conforming concave and convex surfaces on the second end surface of the first endplate and the first end surface of the cap can be inverted to be conforming convex and concave surfaces without affecting joint motion and are included as another embodiment of the invention.

For the sake of clarity, the first end 100 is that end of the device nearest the top of the first end plate 1-1 and the second end 200 is that end nearest the bottom of a second endplate embodiment. Thus, reference to a first or second end surface in the application refers to that surface closest to the top or bottom end of the device. Thus, for example, the second end surface of a first end plate would be facing the first end surface of a second end plate.

The present invention is more particularly described in the following embodiments and examples that are intended to be illustrative only since modifications and variations therein will be apparent to those skilled in the art. As used in the specification and in the claims, the singular for "a," "an" and "the" include plural referents unless the context clearly dictates otherwise.

The various embodiments disclosed herein can allow up to six independent degrees-of-freedom at the center of the Functional Spinal Unit (FSU) workspace. Those degrees of freedom continue to operate until one or more joint limits have been reached. The embodiments of the invention pertaining to approximating the potential motion between two vertebrae in an animal spine can maintain the integrity of the variable intervertebral spacing required during motion. For example, under compression, the intervertebral gap can narrow some and under tension it can widen some.

When appropriately scaled, the invention is capable of tracking FSU workspace movements, within prescribed joint limits, for up to three independent translational and three independent rotational motions of the superior vertebra with respect to the inferior vertebra of the FSU. In a patient, the device of the invention can serve, through appropriate mechanical programming of joint stops and scaling, as a disc prosthesis for an FSU at any point along the spine. In specific embodiments, for example, in a patient, the embodiments of the device, with appropriate joint stops and scaling, can be utilized as a disc prosthesis from the cervical to the lumbar regions of a human patient.

Figure 7:
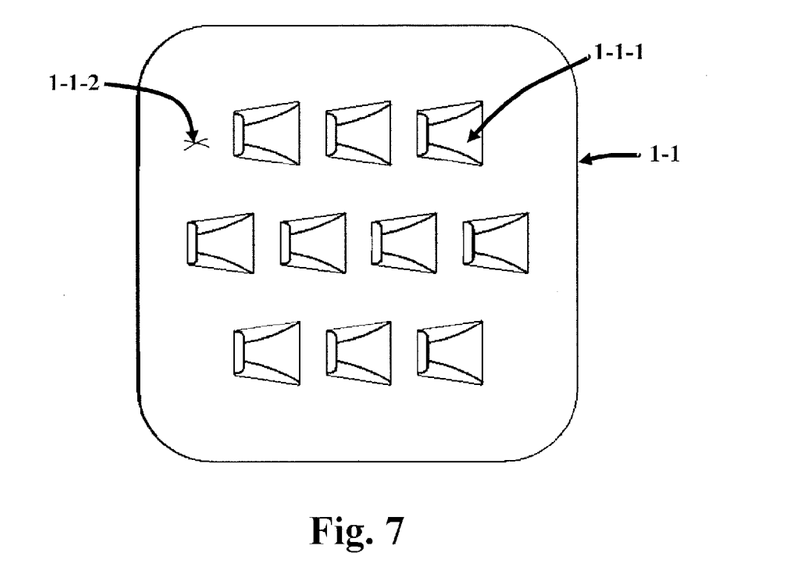
FIG. 7 depicts a top view of a first end surface of an embodiment of a first endplate. In one embodiment. a bottom view of a second end surface of a second endplate can be a mirror image of this view. The anterior portion of the plate is to the left in this view and the posterior portion is to the right, in this embodiment.
Figures 8, 9:
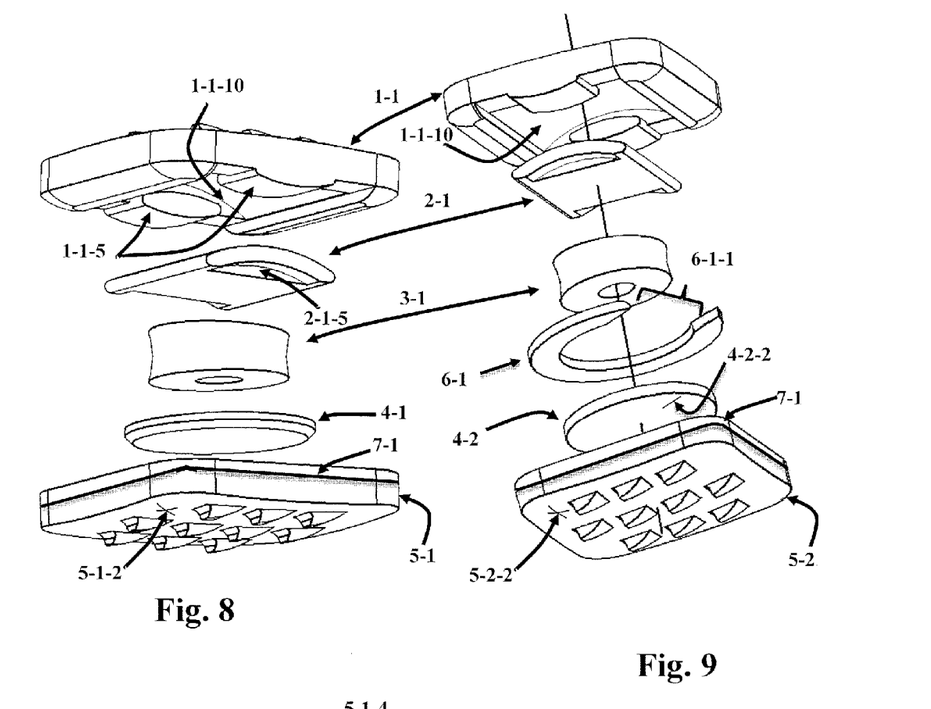

For particular embodiments of the invention, the outside perimeter or circumferential shape, defined by a planar horizontal cross section, of an endplate can be trapezoidal, rectangular, square, rounded-corners square/rectangle, circular, elliptical, or any general closed curve. While these various geometries can affect the shape of the superior and inferior plates, the internal joint mechanism and endplate cavity interfaces can remain essentially the same as described herein. FIG. 7 illustrates an embodiment having a rounded-corners square first and second endplate geometry. It should be understood that one skilled in the art would be able to substitute this circumferential geometry shape with any general closed curve suitable for a particular application. Such variations which perform the same function, in substantially the same way, with substantially the same result are within the scope of the subject invention.

Figure 3:
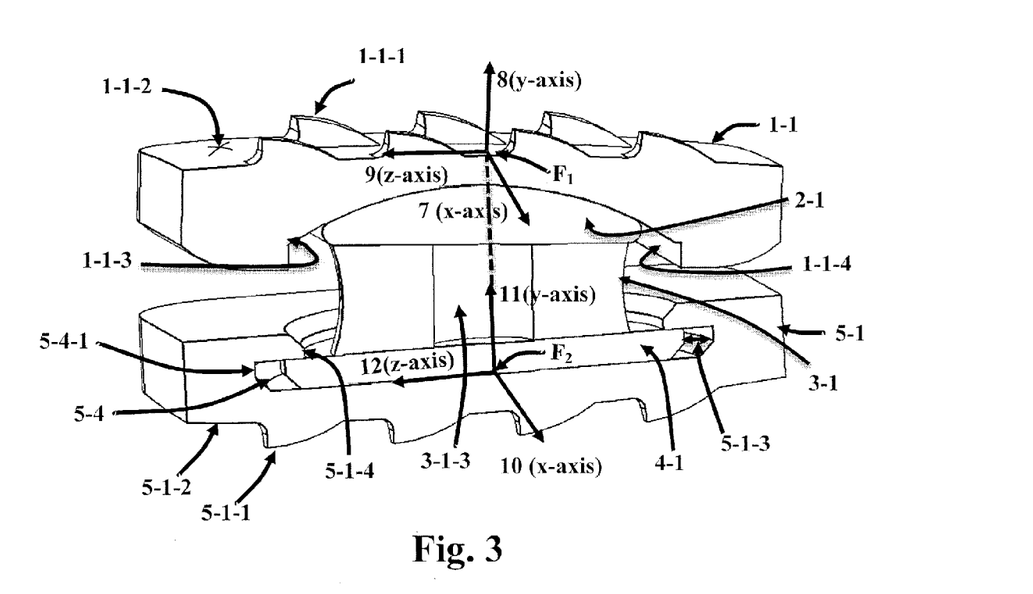
Figure 4:
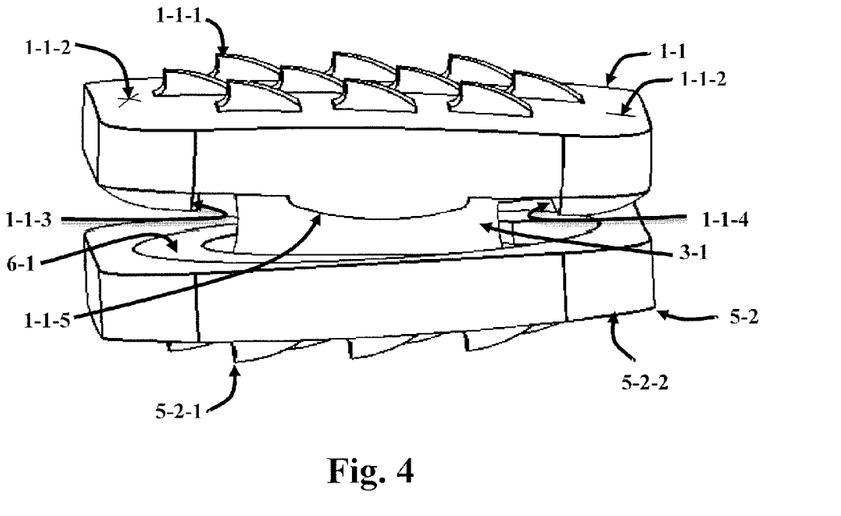
FIG. 4 is an alternative embodiment wherein the sled can be retained in a ring-fitting second end plate 5-2 by a ring 6-1 instead of a snap fit. Ring-fitting second endplate 5-2 differs from the embodiment of a snap-fitting second endplate 5-1 in that a ring-fitting second endplate 5-2 has a recess 5-2-4 (FIG. 20) circumscribing the cavity 5-4 to accommodate a retaining ring 6-1.

As shown in FIG. 3, for this embodiment, the reference frame $F_1$ designates a right-handed coordinate system defined at the centroid of the first endplate first surface and for reference purposes is assumed to be "attached" or anchored to the first endplate. The labels 7, 8, and 9 designate the x-axis, y-axis and z-axis, respectively, and can designate sagittal, vertical, and frontal plane axes, respectively, of frame $F_1$. Coordinates along these axes are designated herein as $x_1$, $y_1$, and $z_1$, respectively. Arrow heads on the axes point in the positive direction. Axis 7 points left-laterally, 8 vertically, and 9 anteriorly.

A second reference frame $F_2$ designates a right-handed coordinate system defined at the centroid of the second endplate first surface cavity and for reference purposes is also assumed to be "attached", or anchored to the second endplate. The labels 10, 11, and 12 designate the x-axis, y-axis and z-axis, respectively, and can designate sagittal, vertical, and frontal plane axes of frame $F_2$. Coordinates along these axes are designated herein as $x_2$, $y_2$, and $z_2$, respectively. Arrow heads on the axes point in a positive direction. Axis 10 points left-laterally, 11 vertically, and 12 anteriorly.

The relative motion between these two frames can be determined from the amount of rotation of the first endplate (a "rigid-body" joint), the compression, extension and lateral flexing of the core (a "continuum" joint) and the sliding and rotating of the sled (a "rigid-body" joint). All relative motions of the first endplate frame $F_1$ with respect to the second endplate can be described with reference to frame $F_2$.

The angle between axes 9 and 12, i.e., the z-axes in each frame, equals the "lordosis angle, $\lambda$," by construction.

FSU angular and translational displacement along the various degrees of freedom, as instructed in the following description and examples, typically relate to cervical spine applications of the invention in a human patient. However, it should be understood that the invention is not restricted to the cervical spine and can be scaled for larger FSUs, for example, L4-L5 in the lumbar region. Further, the invention is not limited to use in only a human patient.

One embodiment of the device of the subject invention comprises a first endplate and a second endplate, each with a first and second end surface, a tripartite nucleus 14 comprising a hard, stiff cap, a flexible core, and a hard, stiff sled, and an optional boot between the endplates. In other embodiments, different components of the tripartite nucleus are flexible or hard. For example, the cap and core can be generally flexible, while the sled is substantially rigid. Since the three elements of the nucleus can comprise one or more viscoelastic polymers, "stiff" and "hard" can be relative terms, as all the elements of the nucleus can be flexible to a greater or lesser degree, depending upon design criteria.

Figure 12:
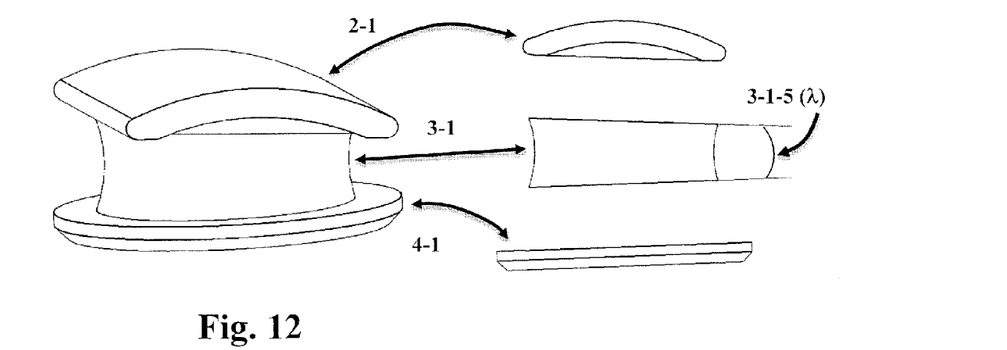
FIG. 12 shows an assembled tripartite nucleus of one embodiment with cap 2-1, core 3-1 and sled 4-1. As indicated by this figure, embodiments of the invention can utilize a nucleus with a solid core and/or a nucleus with the components comprising only one polymer or one or more overmolded or otherwise bonded polymers.
Figures 13, 14:
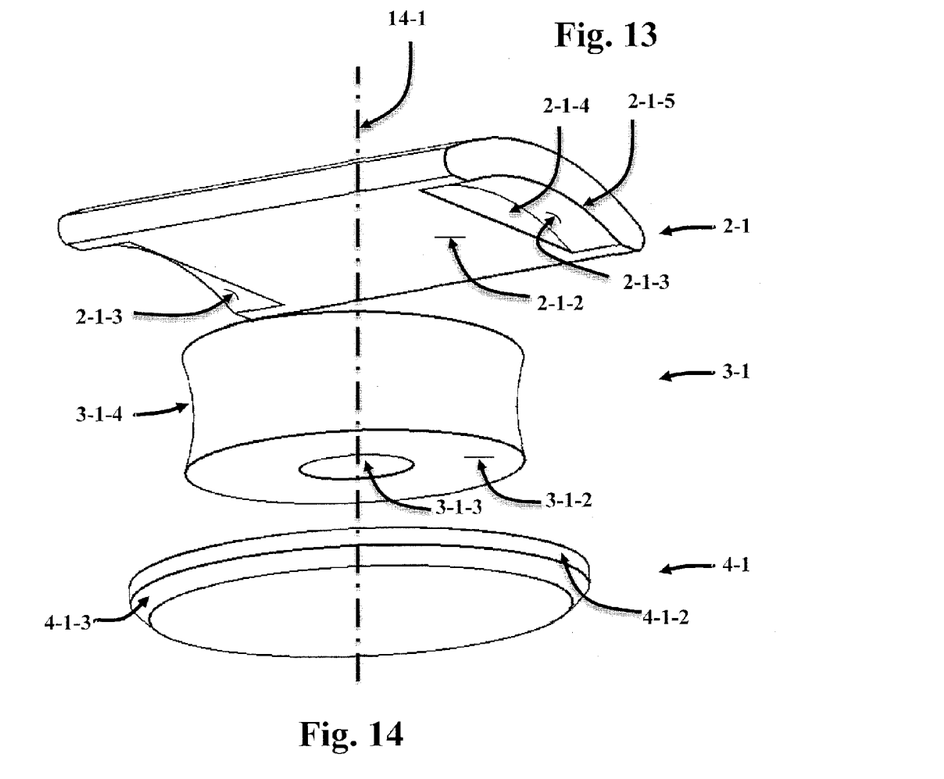
Figure 15:
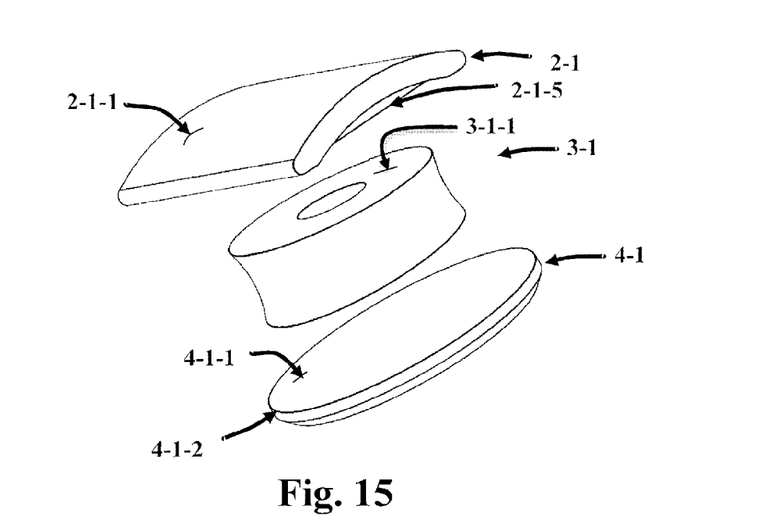
FIG. 15 depicts an exploded perspective view of an embodiment of a tripartite nucleus 14 from above-front-left. The curvate first end surface 2-1-1 of the cap can be a convex surface.

In one embodiment, shown by way of non-limiting example in FIGS. 12-14, the tripartite nucleus 14 can comprise a cap, core, and sled, each with first and second end surfaces and can comprise combinations of materials, both rigid and flexible. For example, the cap and sled can be a polished, hard and tough viscoelastic material. In one embodiment, the cap and sled material have an approximate Shore durometer value of approximately 75D or greater. In a further embodiment, the core can be a softer, more flexible viscoelastic material. In one embodiment, the core material has an approximate Shore durometer value of between approximately 55D and approximately 80D. A thermoplastic nucleus can be graded at interfaces between cap-core and core-sled, such that the material of each component intermingles or mixes to secure the components. Alternatively, the nucleus can comprise a single integrated viscoelastic polymer of one material and hardness, such that the nucleus is a single structure of substantially homogeneous material. In one embodiment, a single integrated viscoelastic polymer has a Shore durometer from approximately 55D to approximately 75D. Variations of thermoplastic composition of the nucleus structure are disclosed in U.S. patent application Ser. No. 13/934,814 (Doty), which is hereby incorporated by reference with regard to such teachings.

Thus, the nucleus can have many operational features and, in a specific embodiment, can comprise three distinct, operably attached components. In a further specific embodiment, a thermoplastic cap, core, and sled can be over-molded, or thermoplastically welded, with or without mechanical interlocks, or otherwise fixedly joined together at adjoining interfaces, to create an integrated, tripartite construction. In another embodiment, the three elements can be fitted or bonded together by adhesives and/or mechanical interlocks. In one embodiment, the components comprise compatible polymer elements that can be over-molded. In a further embodiment, the elements can comprise a single polymer molded as a unified nucleus. Alternative methods of fixedly attaching the nucleus elements would be known to those with skill in the art and are within the scope of the subject invention.

A particular nucleus embodiment can have 1) a cap comprising one or more multi-convex and multi-concave curvate turning surfaces that can have the same center of curvature, but different radii of curvature, 2) a core that can be relatively more compressible and flexible than the cap and the sled, and 3) a transport sled. Embodiments of the sled can provide one or more degrees of freedom, such that there is at least one rotational degree of freedom and/or at least one translational degree of freedom. Alternatively, the sled can be fixed by construction and/or one or more joint stops such that the sled provides no degrees of freedom.

A nucleus cap, core, and sled can each comprise, in a particular embodiment, different layers of viscoelastic or elastomeric polymers with different mechanical properties.

Another particular embodiment can possess non-isotropic transition regions between cap and core and between the core and sled, making a total of five identifiable regions of potentially different compositions. The non-isotropic transition regions can extend over a distance equal to or greater than the nominal thickness of simple adhesive bonding and can also be a graded mix of the polymers used at either side of the transition region. Thermoplastic welding, for example, can create such transition regions. Thermoplastic polymer bonding of the tripartite elements can be advantageous over usual abrupt interface transitions that use adhesive and/or mechanical bonding. It would be within the skill of a person trained in the art to determine bonding variations, including combinations, of such fixing techniques. Such variations which provide the same function, in substantially the same way, with substantially the same result are within the scope of the subject invention.

In a particular embodiment, the cap and sled consist of a thermoplastic material with an approximate Shore durometer of 75D. In a further embodiment, the core can be a flexible thermoplastic material with an approximate Shore durometer ranging from between approximately 60A and approximately 90A. In an alternative embodiment, the entire nucleus can be a thermoplastic material having a Shore durometer value ranging from between approximately 55D to approximately 75D.

By appropriate shaping of the core element of the tripartite nucleus 14, a range of lordosis angles λ (as indicated in FIG. 13) between the first and second endplate can be achieved without changing any of the other parameters of the device. By way of example, the first and second end surfaces of a core can be planar and the plane of those surfaces can be parallel or intersecting. When the two end planes are parallel, the lordosis angle of the device is zero, when the two planes intersect; the lordosis angle of the device is the angle between the planes. FIG. 13 illustrates this angle. By appropriate pitch of the first and second end plates of the core, the lordosis λ of the device can range from zero (when the planes of the endplates are parallel) up to six degrees or more (when the planes of the endplates intersect at six degrees or more). Thus, there can be an infinite number of core nuclei, depending on the degree of lordosis λ chosen for the device core. Thus, the pitch of the end plates of a core can provide any lordosis λ between 0 degrees and approximately 7 degrees. In practice, it is possible for just a small subset of these lordosis angles to be used; for example, the lordosis angle can be selected from 0°, 1.0°, 1.5°, 2.0°, 2.5°, 3.0°, 3.5°, 4.0°, 4.5°, 5.0°, 5.5°, 6.0°, or 6.5°.

In a particular embodiment, the nucleus has a flexible core that is solid, without cavities or channels. A solid core is not shown in the figures, but can be easily understood by a person skilled in the art having benefit of the description and figures of the subject application. In an alternative embodiment, a core possesses an interior void or bore 3-1-3. In a further particular embodiment, the bore is curvate. In another alternative embodiment, shown, for example, in FIG. 16 and FIG. 17, a plurality of channels 3-2-1 lead away from the central bore 3-1-3 to the first and second end planes of the core and also the curvate lateral surfaces of the core. Core channels 3-2-1 exiting at the end plane surfaces can connect to channels 2-2-1 and 4-3-1, shown by way of example, in FIGS. 16 and 17, within cap and sled, respectively, which leads to the mechanical joint surfaces of the device. The bore can be centralized within the core. Alternatively, the bore can be offset from the center of the core.

The first end plate 1-1 and embodiments of the second endplate, 5-1, 5-2, or 5-3, and their respective first and second end surfaces can possess surface features to hold the implant in place. A variety of surface features and treatments, known to those with skill in the art, can be used to assist in fusing the endplate surfaces to vertebral bone, after the device is implanted into an FSU. Ideally, the first surface of a first endplate can fuse to a first vertebra and a second surface of a second endplate can fuse to a second vertebra of an FSU. When spinal muscles dictate complex motion of the first vertebra of the FSU, the first end plate follows the same motion trajectory as the first vertebra, since they are fused together. The resulting motion of the first endplate produced by the hybrid mechanical structure of the subject invention, utilizing a rigid-body revolute joint (between the cap and first endplate), a rigid-body planar joint (between the sled and the second end plate), and a compressible, extensible and flexible core can be completely general. The flexible core can permit an infinite number of possible motions. In particular, compression, extension, lateral bending, and torsion resistance, and combinations thereof, are possible. This hybrid mechanical structure can generate more than six degrees of freedom because of the continuum joint realized by use of the core. Typically, a maximum of six of these degrees of freedom can be independent; the other freedoms, while redundant, assist in the generation of natural motion of the FSU.

FIG. 1, FIG. 2, FIG. 3, FIG. 4, FIG. 5, and FIG. 6 represent specific embodiments of the subject invention. In one embodiment, a boot can be utilized to join the first and second endplates. The boot can provide protection of the nucleus from environmental chemistry; retain normal saline or other biocompatible fluids within the enclosed volume defined by the boot and the first and second endplates; and provide some torsional and extension resistance. In a particular embodiment, the first and second endplates are an F136 titanium alloy. In a further particular embodiment, the cap and sled are Bionate® 75D. And in a still further particular embodiment, the flexible core is Bionate® 80A or 90A or 55D. In another embodiment, the entire nucleus can be Bionate® 75D or 55D. In this case, the cap, core, and sled can have the same constituent mechanical properties. However, it should be understood that any of a wide variety of elastomers and viscoelastic materials can be selected for the cap, core, and sled and the invention is not limited to any specific materials suggested herein. Thus, a person with skill in the art would be able to determine any of a variety of materials that would be suitable for use with the embodiments of the subject invention. Such variations are within the scope of the subject invention.

In one embodiment, the first surface of the first endplate, treated with an bone-fixing coating such as a titanium trabecular mesh, fixedly attaches to a first vertebra in a Functional Spinal Unit (FSU) and the second surface of the second endplate, treated with an bone-fixing coating such as a titanium trabecular mesh, fixedly attaches to a second vertebra in an FSU, such that the spinal disc replacement device of the subject invention is retained between a first and second vertebra. Additionally, projections 1-1-1 and 5-1-1 penetrate vertebral bone to help fix and stabilize the device within the FSU.

The surfaces of the first and second endplates can be curvate to conform to the shape of a natural disc cavity. In the embodiment shown in FIG. 2 and FIG. 3, first surface 1-1-2 of the first endplate 1-1 fixedly attaches to a caudal surface of a first vertebra in a Functional Spinal Unit (FSU) and the second surface 5-1-2 of the second endplate 5-1 fixedly attaches to an anterior surface of a second vertebra in an FSU. These surfaces can be curvate to conform to the natural disc cavity at each of the vertebral surfaces In another embodiment, the nucleus comprises a cap, a core, and a sled, each with a first and second end surface, wherein the second end surface of the cap fixedly attaches to the first end surface of the core, whose second end surface fixedly attaches to the first end surface of the sled. A portion of a second end surface of the cap, the first and second end surface of a core, and the first end surface of a sled can all be planar. Fixing these interfaces can be achieved by thermoplastic welding when the materials are thermoplastic polymers. In such cases, the planarity of the aforementioned surface may not be critical. Mechanical and adhesive bonding can also be employed. Under such circumstance the nature of the bonding surfaces can be scored, dimpled, roughened or otherwise made unsmooth, to allow interstitial adhesion. Finally, the aforementioned planar surfaces can become abstract entities when a nucleus is molded from a single polymer.

A cap second end surface, a core first and second end surfaces, and a sled first and second end surfaces can all be planar. In one embodiment, a cap comprises a multi-curvate and multi-convex first end surface. In a particular embodiment, all convex and concave surfaces have the same center of curvature, but can have different radii of curvature. A second end surface of a first endplate can have multi-curvate, multi-concave, and multi-convex surfaces that conform and mate to the first end surface and second end surface of the cap to form a mechanical joint that can produce one degree of rotational freedom. The convex and concave surfaces of the first endplate and the cap can be so configured such that the first endplate and the cap do not separate once assembled.

The planar interfaces between the cap and the core and the core and the sled can be non-existent in the case of a single material being used for the nucleus, or they can be graded interfaces, such that the material of the core transitions into the material of the cap. Likewise, the material of the core can transition into the material of the sled. In other words, the interface between the cap and core and the core and the sled can be a mixture of the materials utilized for each component.

In certain embodiments, the material properties of the first endplate 1-1 second surface and the first surface of the cap 2-1 can be sufficiently hard and durable so as to be considered a rigid-body rotational joint under nominal operation. In certain other embodiments, the constitutive properties of the materials of the interfacing surfaces do not affect motion in a significant way.

Figure 5:
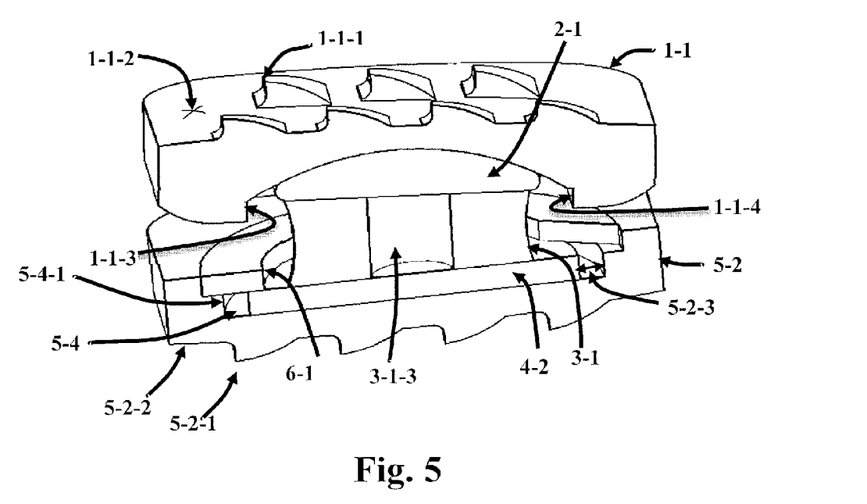
FIG. 5 illustrates, by means of a central sagittal-plane cross-sectional view, a retaining ring 6-1 seated into a recess 5-2-4 within the first end surface of second endplate 5-2 and thereby retain the sled 4-2. The radial translation motion 5-2-3 and rotation motion of the sled 4-2, as well as the first end plate 1-1, the cap 2-1, and the core 3-1 are identical to those used for a snap-fitting second endplate, as shown in FIG. 3.
Figure 10:
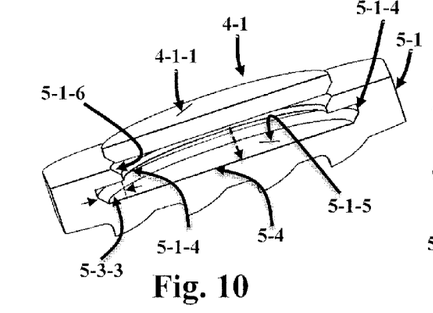
FIG. 10 details a snap fit embodiment of the sled 4-1 into the snap-fitting second endplate 5-1. In this embodiment, sled 4-1 has a first planar surface and a second planar surface with a perimeter chamfer 4-1-3 (refer to FIG. 14). A cavity 5-4 opening in the first end surface of the snap-fitting second endplate 5-1 has a recess 5-3-3 and a planar surface 5-1-5 that can permit the sled to have translational and/or rotational motion. A lateral boundary 5-4-1 of the cavity is located within the recess.
Figure 11:
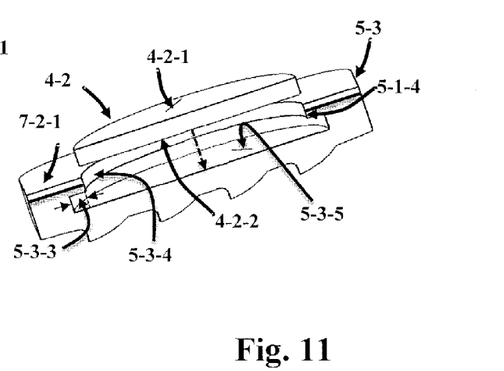
FIG. 11 shows details of the press fit embodiment of sled 4-2 into press-fitting second endplate 5-3 embodiment. In this embodiment, the sled 4-2 has a first planar surface 4-2-1 and a second planar surface 4-2-2. A cavity opening 5-1-4 that opens onto the first end surface of the second endplate 5-3 can have a recess 5-3-3 and a planar surface 5-3-5 that can permit translational and/or rotational motion.

A first end surface of a second endplate 5-1, 5-2, or 5-3, can have a cavity 5-4 therein, as seen, for example, in FIGS. 3, 5, and 10, with a planar surface 5-3-5 that can mate to the second end surface of a sled 4-1, so as to provide at least one translational degree of freedom. In one embodiment, the mating of the sled to the planar surface in the cavity can provide up to two translational degrees of freedom and one rotational degree of freedom.

The material properties of the first surface of a second endplate and the second surface of the sled can be hard and durable, so as to be considered a rigid-body planar joint under nominal operation. In certain other embodiments, the constitutive properties of the materials of interfacing surfaces do not affect motion in a significant way.

In one embodiment, the sled 4-1 of a nucleus 14 has a first and a second end surface that are planar. The first planar end surface of the sled can be fixed or bonded to the second planar end surface of the core. This can be accomplished by, for example, thermoplastic welding or the use of mechanical and adhesive techniques, as discussed previously. The circumferential shape of the lateral surfaces of the sled can be, in general, a closed curve. In particular embodiments, the shape of this closed curve is a circle, a rounded-cornered square, or an ellipsoid.

In a further embodiment, the sled fits into an accommodating cavity 5-4 in the second endplate that opens onto the second end surface. The planar second end surface of the sled 4-1 can conform to a planar surface 5-3-5 in the second endplate cavity. The cavity 5-4 in the second end plate has a recess 5-3-3 in which at least one lateral boundary 5-4-1 is disposed. The peripheral edge 4-1-2 of a sled and the lateral boundary of an endplate cavity can have general, curvate shapes, where the cavity boundary can have a variable, curvate offset from the sled boundary.

In a particular embodiment, the sled peripheral edge 4-1-2 is a circle and the second endplate cavity lateral boundary 5-4-1 a circle of the same or, alternatively, a larger radius. In this embodiment the boundary offset of the two curves is the difference between the cavity lateral boundary and the sled peripheral edge radii. Thus, in an embodiment, where the radii difference equals zero, the peripheral edge 4-1-2 of the sled and lateral boundary 5-4-1 of the cavity are substantially abutted on all sides, such that the sled can only rotate within the cavity, since there is no space for translation. In an embodiment where the radii difference is greater than zero, the lateral boundary and peripheral edge do not abut on all sides, so the sled can have up to three degrees of freedom, two translational and one rotational. The translation range can be bounded by the difference in radii in any direction, as measured when the sled starts from the cavity center.

In another embodiment, a sled peripheral edge 4-1-2 is a circle and the second endplate cavity lateral boundary 5-4-1 is a rounded-corner rectangle whose rounded corners can have the same radius of curvature as the sled and whose width equals the diameter of the sled, thus restricting motion in that direction. and whose length can be larger than the diameter of the sled. In such an embodiment, the sled has only one degree of translational freedom, that being along the length of the rectangular space, and one degree of rotational freedom, that being about axis 14-1. The range of translation of the sled will be dictated by the diameter of the sled and the length of the rectangular cavity. This configuration limits rotations of the sled joint to those about the axis 14-1, which passes through the center of the sled perpendicular to the second plane of the sled. In this embodiment, these rotations are not constrained by the sled-endplate interface.

In yet another embodiment, both the sled peripheral edge 4-1-2 and the second endplate cavity lateral boundary 5-4-1 have a rounded-corners rectangle shape with corners of the same radii of curvature. The difference in length (width) of the sled rectangle and the length (width) of the larger second endplate cavity rectangle determines the range of motion of the sled in a direction parallel to its length (width). In one embodiment, a circumscribing circle of the sled boundary lies wholly within the cavity boundary for a given position of the sled, allowing the sled to rotate unconstrained in the cavity while in that position. Alternatively, rotations of the sled are limited to a value dictated by the current position of the sled; the diagonal length of the sled, and the width of the cavity.

In general, from the peripheral edge geometries of a sled and the lateral boundary of the second endplate cavity, the associated range of motion of the sled within the second endplate cavity can be determined by one skilled in the art and can be mechanically programmed to meet requirements of a particular client.

Figure 1:
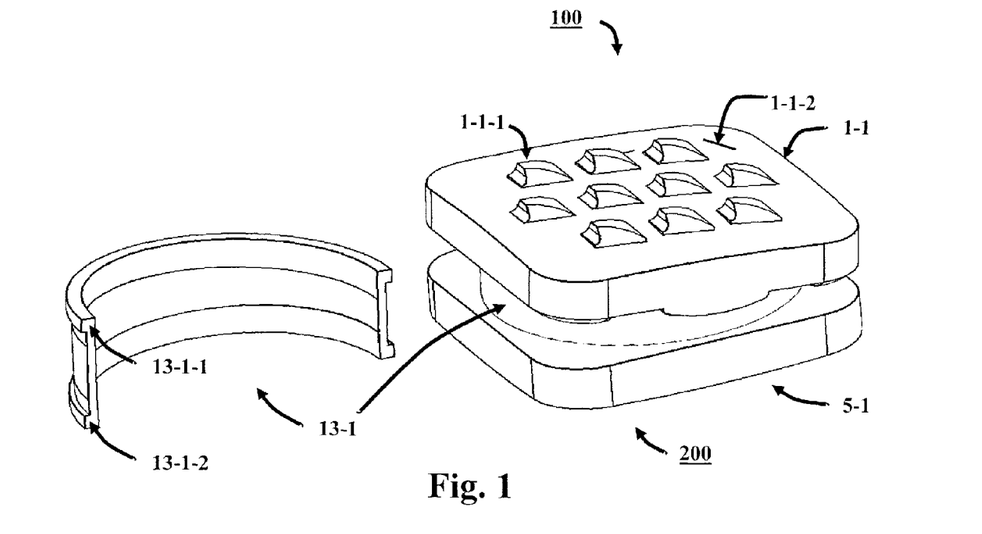
Figure 2:
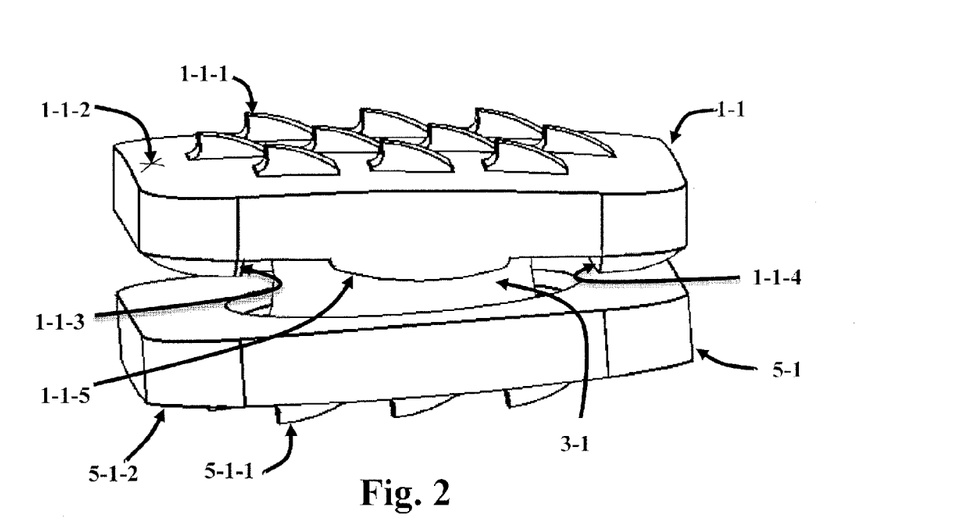
Figure 16:
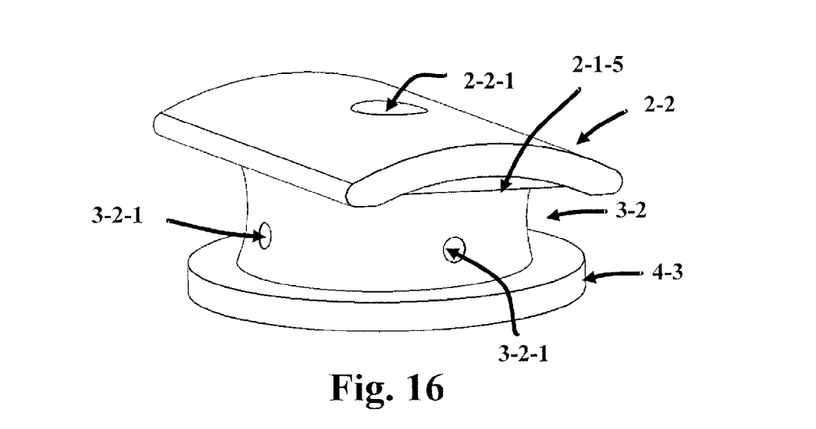
FIG. 16 illustrates an embodiment of a tripartite nucleus 14 whose core 3-2 can have a plurality of hydraulic channels 3-2-1 and whose cap 2-2 can have a through channel 2-2-1.
Figure 17:
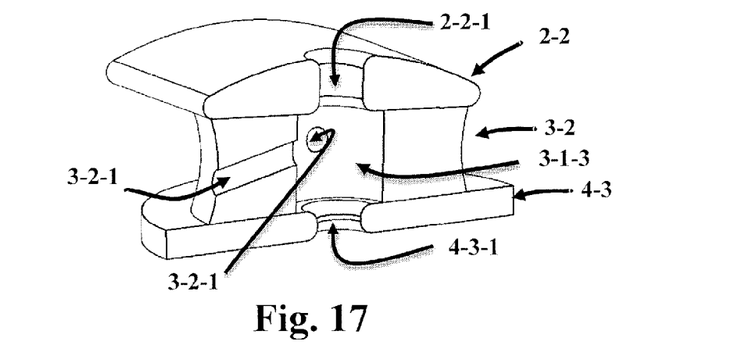
FIG. 17 represents a central sagittal plane cross-section of the tripartite nucleus embodiment shown in FIG. 16, exposing the bore 3-2-2 and hydraulic channels 3-2-1 and through channel 4-3-1 of sled 4-3.

Particular embodiments of a flexible core 3-1 can support a plurality of hydraulic channels 3-2-1 emanating from a central bore 3-1-3 in the core that can assist in shock absorption and damping and can provide lubricious joint operation by forcing fluids between the sliding and rotating surfaces (refer to FIG. 16 and FIG. 17). In a particular embodiment, a hydraulic fluid is a sterile, normal saline solution encapsulated by a boot 13-1 (FIG. 1). In an alternative embodiment, there is no boot (FIG. 2) around the nucleus. Thus, in this embodiment, the hydraulic fluids are biological or environmental fluids around the implanted device. In another embodiment, one or more duckbill valves, or other valves or valving techniques, are located at the openings of hydraulic channels within the hydraulic bore 3-1-3, here shown central to the core. The valves can allow fluid to flow into the chamber, but not out of the chamber. Duckbill valves, or other valving techniques, can also establish one-way flow out of the central bore through a top portal 2-2-1 and a bottom portal 4-3-1, which lead to the respective rotation and planar joints. Such a configuration, during operation, can supply "synovial-like" lubricious action for sliding surfaces, thus, reducing wear and friction in the mechanical joints. As mentioned previously, while the core can have a bore 3-1-3 in particular embodiments, shown in the diagrams herein, this is not essential. In other embodiments the core can be solid and without a bore, as was mentioned previously. An embodiment of the core without a bore is not depicted within the figures. But, it would be within the skill of a person trained in the art to understand that the core can be solid or substantially contiguous.

Particular embodiments of a nucleus comprise a structure having a cap 2-1 (without a top portal 2-2-1) or cap 2-2 (with a top portal 2-2-1), a core 3-1 (here shown with a central bore), or core 3-2 (here shown with a central bore and hydraulic channels), and a sled 4-1 (with a chamfered second end surface), a sled 4-2 (with peripheral edge 4-1-2 that is flat), and a sled 4-3 (having a bottom portal 4-3-1). Not all such arrangements have the same utility and other embodiments might differ significantly, but all configurations can produce the same functionality with regard to relative motion between the first and second endplates and maintain the appropriate lordosis λ, dictated by the slope of the first and second end surfaces of the core, as discussed above.

Figure 6:
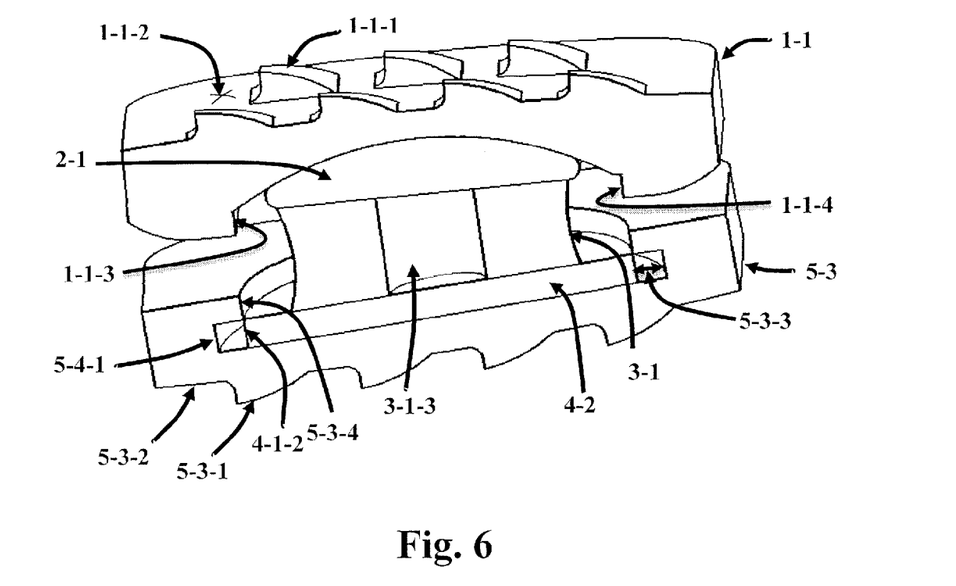
FIG. 6 discloses yet another alternative embodiment wherein the sled press fits into the cavity of a press-fitting second endplate 5-3. In this embodiment, to slideably and rotationally lock the sled into the cavity within the first end surface of the press-fitting second endplate, a tight fit is required to insert and extract the sled from its cavity. Once inserted, however, the sled can be free to move and rotate in the cavity within the press-fitting second endplate first end surface.

In one embodiment, a nucleus comprising: cap 2-1, core 3-1, and sled 4-1, an example of which is shown in FIG. 3 and FIG. 12; cap 2-1, core 3-1, and sled 4-2, as shown, for example, in FIG. 5 and FIG. 6; and cap 2-2, core 3-2, and sled 4-3, as shown, for example, in FIG. 17 all allow the same motion functionality. Another nucleus embodiment can comprise a sled similar to 4-1, but with a bottom portal 4-3-1 that can be joined advantageously with core 3-2.

In a particular embodiment, portion 2-1-2 of the second end surface of a cap, the first and second end surface of the core, 3-1-1 and 3-1-2, respectively, and the first end surface of a sled 4-1-1 are all planar.

Figure 18:
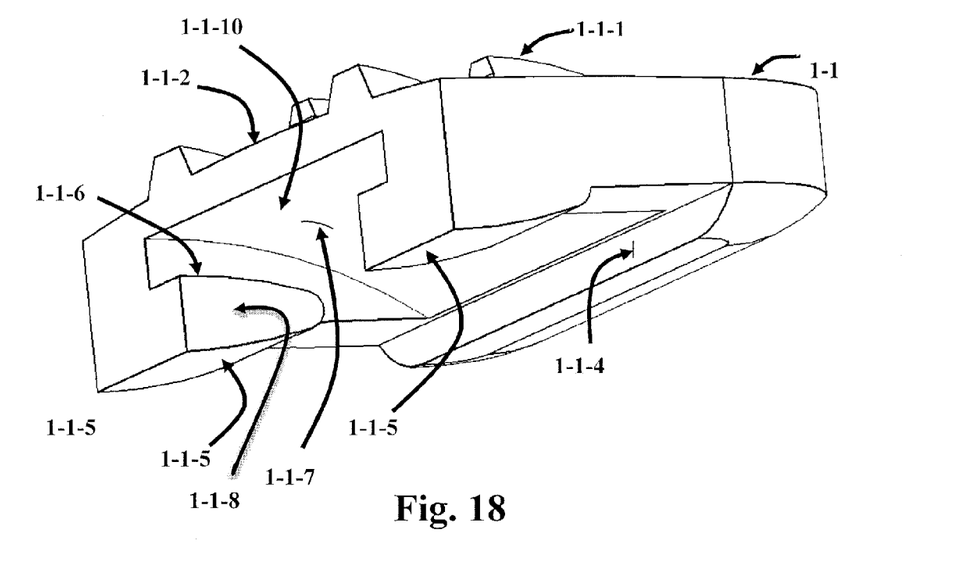
FIG. 18 shows a central frontal plane cross-section of a particular embodiment of a first endplate to illustrate the various surfaces thereof. In this embodiment, the interior end surfaces 1-1-6 of the retaining features 1-1-5 are convex and conform to a concave surface 2-1-3 on the cap. Rotation joint stop 1-1-4 can limit the amount of flexion rotation. Joint stop 1-1-3, not seen here, can be a mirror image of joint stop 1-1-4 about the cut plane and can limit the amount of extension rotations. Curvate concave chamber 1-1-10 has a surface 1-1-7 that can accommodate a curvate convex surface 2-1-1 of the first end surface of the cap.
Figure 19:
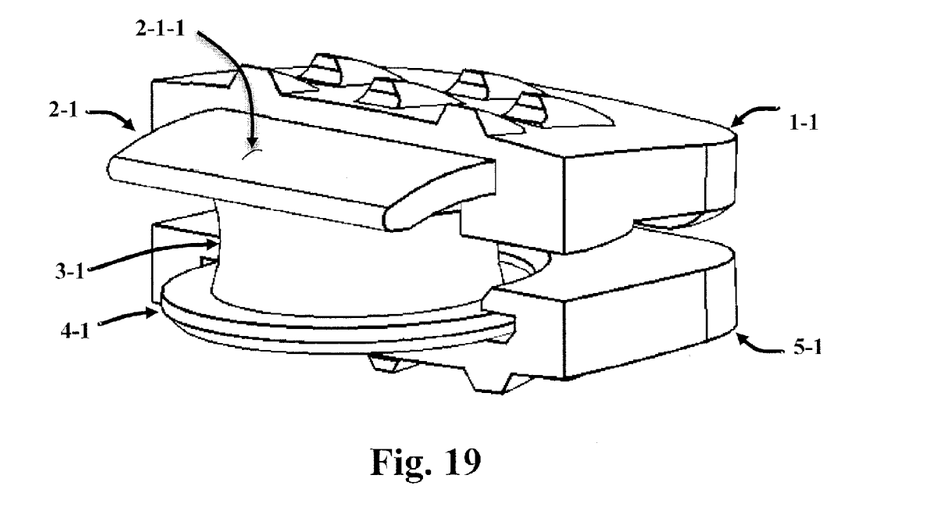
FIG. 19 depicts a central frontal plane partial cross-section of an embodiment of the invention that illustrates the conforming fit of the multi-curvate, multi-convex, multi-concave first end surface of the cap, with the multi-curvate, multi-concave, multi-convex second end surface of the first endplate (FIG. 18). Also shown is an embodiment of the conforming fit between the first and second end surfaces of the sled with the first end surface cavity in the second end plate. The figure also illustrates how the multiple surfaces can enable a rotatable interlock between the first endplate and the cap of an assembled nucleus.
Figure 20:
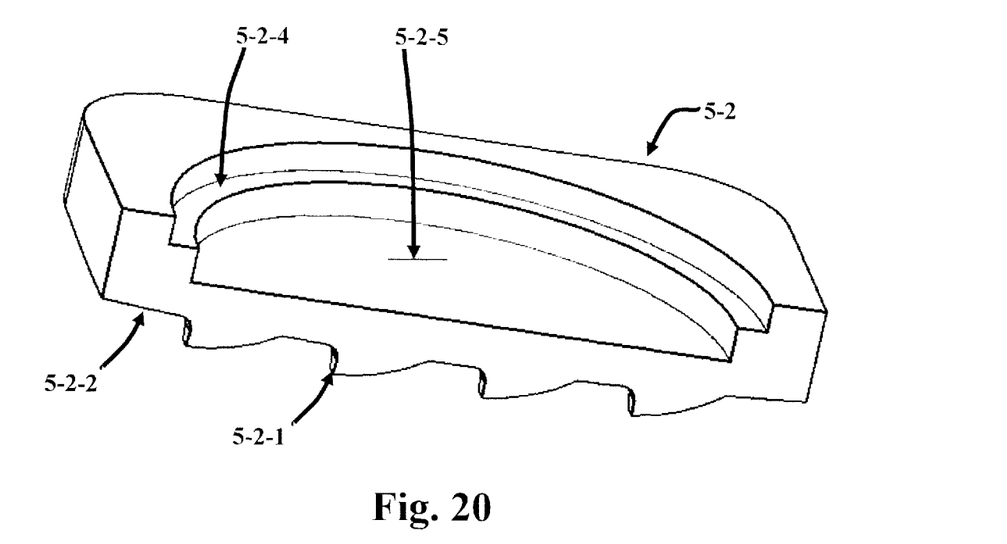
FIG. 20 shows details of an embodiment of a ring-fitted second endplate 5-2 with a curvate second end surface 5-2-2 and cavity 5-4 within the first end surface. Retaining ring recess 5-2-4 circumscribing the cavity 5-4 and planar floor 5-2-5 are principal features of this cavity embodiment.
Figure 21:
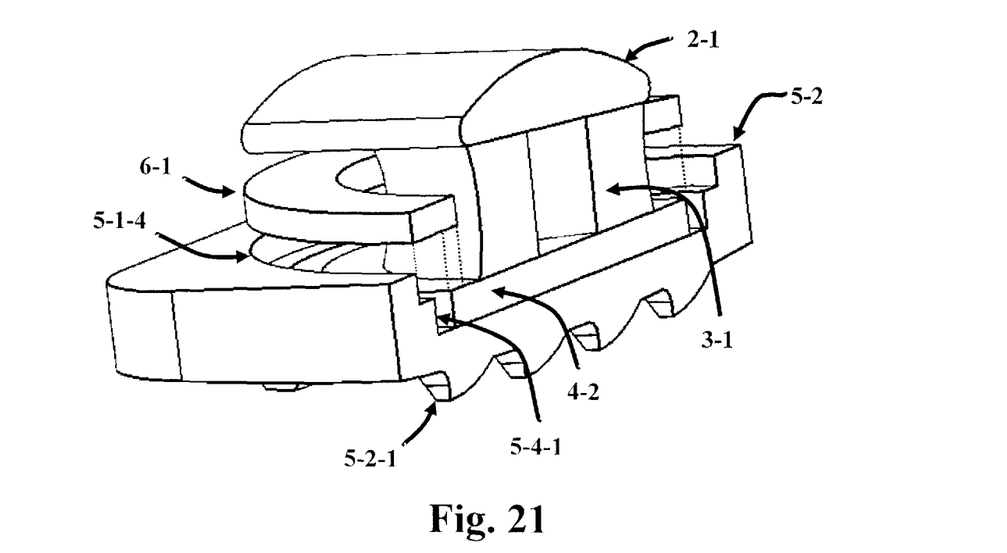
FIG. 21 illustrates an embodiment of the invention that uses a retaining ring 6-1 to prevent withdrawal of the sled of an assembled tripartite nucleus 14 from the cavity 5-4 in a ring-fitted second endplate 5-2. In a particular embodiment, approximately 270° of the ring inner diameter can overlap a portion of the sled's planar first end surface for all positions of the sled in the cavity. This provides an aperture 6-1-1 comprising approximately 90° of the ring diameter, which can be sufficient for a core to pass through so as to be situated within the center of the retaining ring.

A second end surface of a cap can comprise a combination of a planar section and at least one lateral notch having a multi-concave and vertical planar surface. An example of such an embodiment of a second end cap surface is shown in FIG. 14 and has planar section 2-1-2, and lateral notches formed by two concave cylindrical sections 2-1-3 and two vertical planar sections 2-1-4 with an arcuate boundary corresponding to the concave cylindrical section. When the notch on the second end surface of such a cap mates (FIG. 19) with a retaining feature 1-1-5 interior end surface 1-1-6 (twice, one on each lateral side), 1-1-8 (twice, one on each lateral side) and curvate surface 1-1-7 (FIG. 18) that conforms to it, the combination provides a rotational joint with at least one degree of rotation freedom about a sagittal direction. In a specific embodiment, the cap rotates in an anterior to posterior direction. The center of rotation of this joint equals the common center of curvature for surfaces 1-1-6, 1-1-7, 2-1-1, and 2-1-3 and its axis of rotation is a line perpendicular to the sagittal plane that passes through this center of rotation. This arrangement of cap and first endplate surfaces provides a kinematic interlock between them without requiring external forces to maintain the interlock, once the device is assembled. This arrangement makes the top joint a closed-profile joint. The inclusion of an extension rotational joint stop 1-1-3 and a flexion rotational joint stop 1-1-4 can limit flexion-extension rotations to operate within nominal bounds and can reduce hyper-mobility of an FSU.

In one embodiment, the second end surface of the sled is planar and fits into a cavity of the first end surface of the second endplate wherein the cavity has a planar floor and is larger than the sled in one or two orthogonal dimensions. Together, the sled and the second endplate provide up to one degree of rotational freedom about the central axis of the sled, or one degree of translational freedom, or one degree of translational freedom combined with one degree of rotational freedom, or two independent degrees of translational freedom and one of axial rotation. Variable offset distances between the sled peripheral edge and the receiving cavity lateral boundary in the second endplate allows mechanical programming of the planar joint motion in complex ways. A simple rounded-corners square/rectangle sled and cavity boundaries illustrate this idea.

A sled can be disc shape, such as sled 4-1, sled 4-2, and sled 4-3, and can fit into a larger receiving cavity 5-4 in the first end surface of the herein described embodiments of the second end plate 5-1, 5-2, or 5-3. The nature of the sled and receiving cavity boundaries can also dictate the range of motion possible for the sled.

The receiving cavity can also be disc shaped, as shown in FIG. 3, FIG. 5, FIG. 6, FIG. 10, and FIG. 11. For these particular embodiments, the translational motion of the sled can be approximately 1 mm in any direction when centered in the cavity and the sled can rotate about its central axis without interference anywhere it is located within the cavity. The central axis 14-1 of the sled can also coincide with the y-axis 11 of fixed frame $F_2$ when the sled is centered in the receiving cavity of the second endplate, regardless of the sled and receiving cavity shapes.

In another embodiment, the sled and second endplate receiving cavity is a rounded-corners square/rectangle. The rounded corners for both sled and cavity can have the same radius of curvature so that when the sled translates into a corner of the cavity the contours of the two corners conform and the contact between the cavity wall corner and the sled corner involves a surface.

In a specific embodiment, if rounded-corner rectangular sled dimensions are w (lateral width) and l (anterior-posterior length) and the corresponding rounded-corner rectangular cavity dimension are W and L, then, for a centered sled, in frame $F_2$ coordinates $(x_2, z_2)$: $x_2=W-w$ and $z_2=L-l$ which describe the maximum sled translation possible in either direction from a center position. Based on these equations, one skilled in the art can make a spectrum of design choices for the sled and second endplate receiving cavity. By way of non-limiting example, for W=w and L=l, the sled cannot move. For W=w and L>l, the sled cannot move in the lateral direction and cannot rotate. It can move anterior-posteriorly along 12. For W>w and L>l, the sled can translate laterally, anterior-posteriorly, and can rotate about its center axis by an amount dictated by the sled's location within the cavity, the radius of curvature of the corners and the geometric dimension of the sled and cavity boundaries.

As the previous paragraphs suggest, the geometry of the sled and its receiving cavity in the second endplate can be general curves whose (possibly variable) offset leads to a plurality of design choices. In all cases, however, sled motion for a given location within the cavity can allow either zero, one, or two degrees of translation with sled y-axis rotation; or zero or one degree of translation with no rotation. With two translational degrees of freedom, theoretically there must be some sled y-axis rotation, however, minor.

Sled and nucleus retention methods in the second endplate, such as the snap-fitting, ring-fitting, and press-fitting embodiments shown in in FIG. 3, FIG. 5, and FIG. 6 indicate only a few retention options. Other elements, such as one or more retention plates 7-1 that weld, or otherwise fixedly attach, to the first end surface second endplate, can create a lip overhanging the cavity opening 5-1-4 and the peripheral edge 4-1-2 of the sled that matches the extent of retention ring 6-1.

In one embodiment, a retention plate can comprise two or more sections 7-1-2 that are fixedly secured over the cavity opening 5-1-4 to secure the sled, which has been disposed within the second endplate cavity. In a further embodiment, the retention plate sections can be designed to inhibit motion of the sled by impinging upon the translation motion of the core. For example, one or more retention plate sections can extend further over the cavity opening than another retention plate section, such that the nucleus can translate less in one direction than in another, thereby correspondingly inhibiting the translation motion of the sled.

There are any of a variety of devices and methods that can be used to not only secure a sled within a second endplate cavity, but which can also control or proscribe the translation and/or rotational capabilities of the nucleus. Such variations which provide the same function, in substantially the same way, with substantially the same result are within the scope of this invention.

The flexion of the nucleus, and especially the core, when comprised of a softer material, can provide compression, that is, translation in an axial direction of the nucleus, and lateral bending, that is, rotation about a frontal axis. By a hybrid combination of mechanical joints described in the previous paragraphs and flexure of the nucleus, the first endplate can move with up to six independent degrees of freedom with respect to the second endplate. Additional redundant flexure degrees of freedom provided by a flexible nucleus or core can enhance the motion performance of the invention.

Nucleus/core flexure can provide shock absorption and torsional shock absorption and additional redundant motion to the first endplate with respect to the second endplate, enhancing its performance under complex motion demands.

A core can have a bore, for example, a central bore, to reduce stiffness or the core can have a combined bore with hydraulic pathways to enhance damping and shock absorption, if design requirements dictate same. Fluid flow can be controlled by valves, such as appropriately placed duckbill valves, if needed. An example of such a core is depicted in FIG. 16 and FIG. 17. Hydraulic channels 3-2-1 carry fluids to and from the central chamber 3-2-1 and supply the rotational and planar joints with fluids through portals 2-2-1 and 4-3-1.

In one specific embodiment, flexion-extension range-of-motion approximately equals 20°; lateral bending range of motion approximately ±10°; and axial rotation is not limited by the invention, but such motion is resisted by frictional forces in the sled and reaction torsional forces in the core.

If physiologic loading on a first endplate exceeds nominal values, the flexible nucleus/core compresses along the central axis of the invention and can possibly twist and bend under higher than normal shear and torsion. When physiologic loading reduces on the first endplate during extension, a flexible nucleus/core expands up to a non-loaded state, at which point it develops tensile strain and resists further motion until the extension joint stop makes a hard stop on continued motion.

Previous spinal implants have been unable to imitate the full six-degrees of motion provided by a normal FSU and at the same time maintain mechanical connectivity (closed-profile joints) without any externally supplied force, such as, for example, gravity and the pull of tendons and muscles of the spine, especially during extension. A closed profile prosthetic device preserves the integrity, stability, and unity of the prosthesis since the first and second endplates are anchored to vertebral bone in the FSU. Advantageously, the devices of the subject invention are not only able to provide up to six-degrees of rotational and translational movement, but can also provide kinematic connectivity (closed profile)between the first and second endplates without sacrificing motion capabilities. The embodiments disclosed herein have linked components that can prevent undesired motion between components. The device of the subject invention provides a simple, but effective fully motion capable spinal implant.

I claim:

1. A prosthetic device comprising:
   a first end plate having,
      a first end surface,
      a second end surface defining a concave chamber;
      a retaining feature extending laterally and partially across the concave chamber;
   a tripartite nucleus comprising,
      a cap rotatably connected to the concave cavity in the first end plate, the cap comprising at least one notch in which the retaining feature is rotatably mated so as to retain the cap in rotational contact with the concave chamber;
      a core having a first end surface and a second end surface, where the cap is located at the first end surface;
      a sled located at the second end surface of the core, where the sled comprises a second planar surface; and
   a second end plate having a first end surface with a cavity therein for receiving and operably retaining the sled, wherein the cavity comprises a surface against which the second planar surface of the sled is moveably mated,
   such that the device provides a kinematic chain of inseparable, articulating components capable of providing at least one independent translational degree of freedom and at least one independent rotational degree of freedom.

2. The prosthetic device according to claim 1, wherein the sled is press-fit into the cavity.

3. The prosthetic device according to claim 1, wherein the sled is snap-fit into the cavity.

4. The prosthetic device according to claim 1, further comprising a recess circumscribing the cavity in the second end plate and a ring that seats within the recess to retain the sled in the cavity, where the ring comprises an aperture for traversing the core.

5. The prosthetic device, according to claim 1, further comprising a retention plate fixedly attached over the cavity in the second end plate to retain the sled in the cavity.

6. The prosthetic device, according to claim 1, wherein the tripartite nucleus comprises at least one non-isotropic transition region.

7. The prosthetic device, according to claim 6, further comprising a bore within the core.

8. The prosthetic device, according to claim 7, further comprising one or more channels extending from the bore.

9. The prosthetic device, according to claim 8, further comprising a boot fixedly attached to the first end plate and the second end plate.

10. The prosthetic device, according to claim 6, wherein the at least one non-isotropic transition region is located in at least one of the area between the cap and the core and between the core and the sled.

11. The prosthetic device, according to claim 1, wherein each of the cap, core and sled comprise a single polymer.

12. The prosthetic device, according to claim 1, wherein the tripartite nucleus comprises a rigid material or a flexible material, or a combination thereof.

13. The prosthetic device, according to claim 1, wherein the tripartite nucleus comprises at least one viscoelastic polymer.

14. The prosthetic device, according to claim 1, wherein the cavity permits at least one of rotational and translational motion to the sled.

15. The prosthetic device, according to claim 14, wherein the cap rotates in an anterior to posterior direction.

16. The prosthetic device, according to claim 15, further comprising one or more joint stops.

17. The prosthetic device, according to claim 1, wherein the core of the tripartite nucleus comprises flexure and shock absorbing characteristics.

18. A method for approximating spinal disc movement comprising:
   implanting within a spine a prosthetic device comprising;
      a first end plate having,
         a first end surface,
         a second end surface with a concave chamber;
         a retaining feature extending from a lateral surface of the second end plate and partially across the concave chamber;
      a tripartite nucleus comprising,
         a cap rotatably connected to the concave cavity in the first end plate, the cap comprising at least one notch in which the retaining feature is rotatably mated so as to retain the cap in rotational contact with the concave chamber;
         a core having a first end surface and a second end surface, where the cap is located at the first end surface;
         a sled located at the second end surface of the core, where the sled comprises a second planar surface; and
      a second end plate having a first end surface with a cavity therein for receiving and operably retaining the sled, wherein the cavity comprises a surface against which the second planar surface of the sled is moveably mated, and a second end surface;
   such that the device when implanted in the spine with the first end surface of the first end plate engaged with a first vertebra and the second end surface on the second end plate engaged with a second vertebrae, provides a kinematic chain of inseparable, articulating components capable of providing at least one independent translational degree of freedom and at least one independent rotational degree of freedom between the vertebra.

19. The method according to claim 18, wherein the prosthetic device further comprises one or more joint stops and the method further comprises adjusting the rotational and translational freedoms using one or more joint stops.

* * * * *